AZALEA PLANT
Filed Nov. 25, 1974
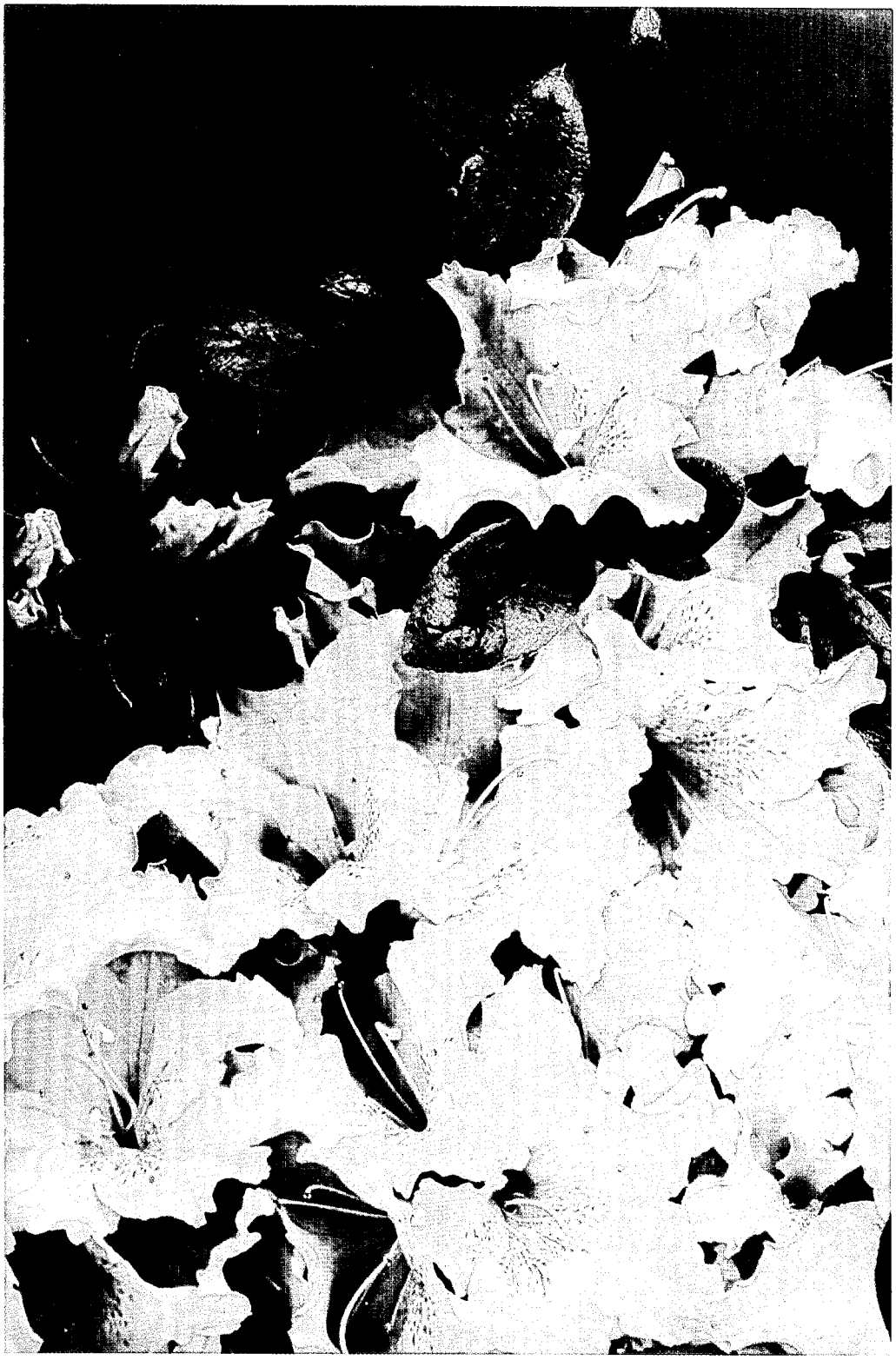

United States Patent

Plant Pat. 3,866

Patented Apr. 20, 1976

3,866

AZALEA PLANT

James W Hines, Jr., Corona Del Mar, Calif., assignor to Hines Wholesale Nurseries, Santa Ana, Calif.

Filed Nov. 25, 1974, Ser. No. 526,620

Int. Cl. A01h *5/00*

U.S. Cl. Plt—56 1 Claim

The present invention relates to a new and distinct variety of azalea plant. This plant was originated by me in March 1957, by crossing the azalea variety of the Southern Indica strain, Azalea "Twilight" (unpatented) with the azalea variety of the Belgian Indica strain, Azalea "Twilight"/Azalea "Wm. Van Orange" (unpatented). The seeds which were produced by this hybridization were first sown in September 1957, and the plant first bloomed in March 1958.

As a result of this breeding, I have produced a new and improved azalea variety which is endowed with the following unique combination of characteristics which are outstanding therein, and which distinguish the same from its parents, as well as from all other varieties of which I am aware.

The plant is characterized as to novelty by its ability to grow and flower in full sun or light shade in the southern California area without tip burning of the leaves or blasting of the flowers; by its abundant and rich green foliage and compact and dense habit of growth; by the unique coloring of its flowers; and by its profuse flowering.

The new variety has been asexually reproduced by me on my cultivated property on the Irvine Ranch, near Santa Ana, Calif. Several hundred cuttings of this new and distinct variety have been made since March 1963, and it holds its distinguishing characteristics through succeeding propagations.

The drawings which accompany this petition show a typical view of the flowers and foliage of my new azalea variety. These are portrayed in color as fairly as can possibly be obtained by this method of illustration.

To facilitate identification of the important colors, I have used the color terminology of the R.H.S. Colour Chart issued by the Royal Horticultural Society of London.

Locality where grown and observed: On the Irvine Ranch, approximately 5 miles south of Santa Ana, Calif.

Parentage: Seedling resulting from planned propagation.

*Seed parent.*—Azalea "Twilight" an unpatented variety of the Southern Indica strain.

*Pollen parent.*—Azalea "Twilight"/Azalea "Wm. Van Orange," an unpatented variety of the Belgian Indica strain.

THE PLANT

Growth: The plant is of very vigorous growth habit, with dense branching starting just above ground level. Flowering is prolific, with first blooms in late November, and heaviest bloom from late February into March. The plant is suitable for forcing. This plant has a stronger growth habit than the Belgian Indica variety, with plants in the nursery growing to a height of three feet.

Branches: New growth is in the Greyed-Orange Group, Plates 164A to 164B, gradually changing color towards the tip to the Yellow-Green Group, Plates 152C to 152D. Older branches are in the Brown Group, Plate 200D. All branches are hirsute.

Foliage: The leaves are of good substance, semi-glossy and abundant.

Shape: Elliptic with an acute tip. Leaf margins are entire and slightly hairy.

Color:

*New Leaves.*—Upper surface is in the Yellow-Green Group, Plates 144A to 144B. Underside is in the Yellow-Green Group, Plates 146B to 146C.

*Mature leaves.*—Upper surface is in the Yellow-Green Group, Plates 147A to 147B. Underside is in the Yellow-Green Group, Plates 146B to 147B.

Size: New leaves range from ¾ to 1 inch in width, and 1¼ to 2 5/16 inches in length. Mature leaves range from ⅞ to 1 inch in width, and 2 to 2⅜ inches in length.

Veins: Prominent and lighter in color than leaf, running from the petiole to the tip, and having lateral veins extending therefrom.

THE FLOWER

The plant first flowers in late November, with heaviest bloom in late February, extending to mid-March, with occasional blooming thereafter. The flowers are borne 2 to 5 to a stem, regularly clustered, with flowers appearing at both the tips of the branches, and also to mid-branch, creating a very floriferous effect.

Form: Flowers are ruffled single.

Petals: 5 in number, and at maturity, blossoms range in size from 3 inches in width, to a depth of 2 to 2¼ inches.

Color: The color of the flowers are in the Red-Purple Group, ranging in shade from Plates 62B to 62D at the crown, to Plates 61B to 61C at the base of the corolla tube, with a fringed edging in the Red-Purple Group, Group, Plates 73C to 73D.

Buds: Long, tapered, and in the Red-Purple Group, shading from Plates 63B and 63C to Plates 62B and 62C.

Reproductive organs:

*Stamens.*—From 6 to 8, with the color in the White Group, Plates 155B to 155C. They range from 1 to 1½ inches in length.

*Pollen.*—Yellow Group, Plates 10B to 10C.

I claim:

1. A new and distinct variety of azalea plant which is a hybrid of the Belgian Indica strain, and the Southern Indica strain, and characterized in particular to novelty by its ability to grow and flower in full sun or light shade in the southern California area without tip burning of the leaves or blasting of the flowers; by its abundant and rich green foliage and compact and dense habit of growth; by the unique coloring of its flowers; and by its profuse flowering; and by its greater salts tolerance, making it less subject to root diseases common to other varieties grown in the same general area of the Irvine Ranch in southern California.

No references cited.

ROBERT E. BAGWILL, Primary Examiner